(12) United States Patent
Morman et al.

(10) Patent No.: US 7,320,948 B2
(45) Date of Patent: Jan. 22, 2008

(54) EXTENSIBLE LAMINATE HAVING IMPROVED STRETCH PROPERTIES AND METHOD FOR MAKING SAME

(75) Inventors: Michael Tod Morman, Alpharetta, GA (US); Sjon-Paul Lee Conyer, Westmoreland, TN (US); Gregory Todd Sudduth, Cumming, GA (US); Randall James Palmer, Acworth, GA (US); David Michael Matela, Alpharetta, GA (US); Prasad Shrikrishna Potnis, Duluth, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 628 days.

(21) Appl. No.: 10/325,470

(22) Filed: Dec. 20, 2002

(65) Prior Publication Data

US 2004/0121687 A1    Jun. 24, 2004

(51) Int. Cl.
 *B32B 27/12* (2006.01)
 *B32B 27/32* (2006.01)
 *B32B 27/00* (2006.01)
(52) U.S. Cl. .................... 442/394; 442/398; 428/424.8
(58) Field of Classification Search ................ 442/394, 442/398
 See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,708,831 A | 1/1973 | Burger |
| 3,802,817 A | 4/1974 | Matsuki et al. |
| 3,849,241 A | 11/1974 | Butin et al. |
| 3,904,465 A | 9/1975 | Haase et al. |
| 4,039,364 A | 8/1977 | Rasmussen |
| 4,100,324 A | 7/1978 | Anderson et al. |
| 4,105,491 A | 8/1978 | Haase et al. |
| 4,111,733 A | 9/1978 | Periers |
| 4,116,892 A | 9/1978 | Schwarz |
| 4,144,008 A | 3/1979 | Schwarz |
| 4,151,245 A | 4/1979 | Suzuki |
| 4,153,664 A | 5/1979 | Sabee |
| 4,153,751 A | 5/1979 | Schwarz |
| 4,209,563 A | 6/1980 | Sisson |
| 4,223,059 A | 9/1980 | Schwarz |
| 4,238,443 A | 12/1980 | Levy |
| 4,251,585 A | 2/1981 | Schwarz |

(Continued)

FOREIGN PATENT DOCUMENTS

EP    0 064 853    11/1982

(Continued)

*Primary Examiner*—Lynda Salvatore
(74) *Attorney, Agent, or Firm*—Pauley Petersen & Erickson

(57) ABSTRACT

An extensible laminate having improved set and hysteresis is disclosed. The extensible laminate includes an extensible nonwoven web laminated to an elastomeric sheet that have been mechanically stretched in the cross direction after lamination. A method for making the extensible laminate includes laminating an extensible nonwoven web to an elastomeric sheet to form a laminate and mechanically stretching the laminate in a cross direction by at least about 50 percent.

46 Claims, 5 Drawing Sheets

U.S. PATENT DOCUMENTS

| | | | |
|---|---|---|---|
| 4,285,100 A | 8/1981 | Schwarz | |
| 4,332,035 A | 6/1982 | Mano | |
| 4,340,563 A | 7/1982 | Appel et al. | |
| 4,368,565 A | 1/1983 | Schwarz | |
| 4,422,892 A | 12/1983 | Plant | |
| 4,475,971 A | 10/1984 | Canterino | |
| 4,517,714 A | 5/1985 | Sneed et al. | |
| 4,629,525 A | 12/1986 | Rasmussen | |
| 4,663,220 A | 5/1987 | Wisneski et al. | |
| 4,704,116 A | 11/1987 | Enloe | |
| 4,720,415 A | 1/1988 | Vander Wielen et al. | |
| 4,741,949 A | 5/1988 | Morman et al. | |
| 4,795,668 A | 1/1989 | Krueger et al. | |
| 4,798,603 A | 1/1989 | Meyer et al. | |
| 4,806,300 A | 2/1989 | Walton et al. | |
| 4,863,785 A | 9/1989 | Berman et al. | |
| 4,910,064 A | 3/1990 | Sabee | |
| 4,965,122 A * | 10/1990 | Morman | 442/328 |
| 4,981,747 A | 1/1991 | Morman | |
| 4,992,124 A | 2/1991 | Kurihara et al. | |
| 5,028,289 A | 7/1991 | Rasmussen | |
| 5,043,036 A | 8/1991 | Swenson | |
| 5,057,368 A | 10/1991 | Largman et al. | |
| 5,064,802 A | 11/1991 | Stevens et al. | |
| 5,069,970 A | 12/1991 | Largman et al. | |
| 5,108,820 A | 4/1992 | Kaneko et al. | |
| 5,114,781 A | 5/1992 | Morman | |
| 5,116,662 A | 5/1992 | Morman | |
| 5,117,540 A | 6/1992 | Walton et al. | |
| 5,156,793 A | 10/1992 | Buell et al. | |
| 5,167,897 A | 12/1992 | Weber et al. | |
| 5,176,668 A | 1/1993 | Bernardin | |
| 5,176,672 A | 1/1993 | Bruemmer et al. | |
| 5,192,606 A | 3/1993 | Proxmire et al. | |
| 5,226,992 A | 7/1993 | Morman | |
| 5,244,716 A | 9/1993 | Thornton et al. | |
| 5,277,976 A | 1/1994 | Hogle et al. | |
| 5,336,545 A | 8/1994 | Morman | |
| 5,336,552 A | 8/1994 | Strack et al. | |
| 5,344,691 A | 9/1994 | Hanschen et al. | |
| 5,374,696 A | 12/1994 | Rosen et al. | |
| 5,382,400 A | 1/1995 | Pike et al. | |
| 5,385,775 A | 1/1995 | Wright | |
| 5,399,219 A | 3/1995 | Roessler et al. | |
| 5,418,045 A | 5/1995 | Pike et al. | |
| 5,422,172 A | 6/1995 | Wu | |
| 5,466,410 A | 11/1995 | Hills | |
| 5,486,166 A | 1/1996 | Bishop et al. | |
| 5,490,846 A | 2/1996 | Ellis et al. | |
| 5,496,429 A | 3/1996 | Hasse et al. | |
| 5,498,468 A | 3/1996 | Blaney | |
| 5,509,915 A | 4/1996 | Hanson et al. | |
| 5,518,801 A | 5/1996 | Chappell et al. | |
| H1558 H | 7/1996 | Goulait et al. | |
| 5,540,796 A | 7/1996 | Fries | |
| 5,547,531 A | 8/1996 | Allen et al. | |
| 5,560,793 A | 10/1996 | Ruscher et al. | |
| 5,595,618 A | 1/1997 | Fries et al. | |
| 5,615,460 A | 4/1997 | Weirich et al. | |
| 5,620,545 A | 4/1997 | Braun et al. | |
| 5,628,097 A | 5/1997 | Benson et al. | |
| 5,628,741 A | 5/1997 | Buell et al. | |
| 5,647,864 A | 7/1997 | Allen et al. | |
| 5,723,087 A | 3/1998 | Chappell et al. | |
| 5,753,343 A | 5/1998 | Braun et al. | |
| 5,861,074 A | 1/1999 | Wu | |
| 5,906,879 A | 5/1999 | Huntoon et al. | |
| 5,914,084 A | 6/1999 | Benson et al. | |
| 5,955,187 A | 9/1999 | McCormack et al. | |
| 6,096,668 A | 8/2000 | Abuto et al. | |
| 6,114,263 A | 9/2000 | Benson et al. | |
| 6,149,637 A | 11/2000 | Allen et al. | |
| 6,203,654 B1 | 3/2001 | McFall et al. | |
| 6,214,274 B1 | 4/2001 | Melius et al. | |
| 6,258,308 B1 | 7/2001 | Brady et al. | |
| 6,264,864 B1 | 7/2001 | Mackay | |
| 6,265,045 B1 | 7/2001 | Mushaben | |
| 6,368,444 B1 | 4/2002 | Jameson et al. | |
| 6,383,431 B1 | 5/2002 | Dobrin et al. | |
| 6,570,056 B1 * | 5/2003 | Tanzer et al. | 604/368 |
| 6,613,954 B1 | 9/2003 | Horney et al. | |
| 2001/0041487 A1 | 11/2001 | Brady et al. | |
| 2001/0042938 A1 | 11/2001 | Mackay | |
| 2002/0016122 A1 * | 2/2002 | Curro et al. | 442/381 |
| 2002/0088534 A1 | 7/2002 | Kobayashi et al. | |
| 2002/0089087 A1 | 7/2002 | Mushaben | |
| 2002/0105110 A1 | 8/2002 | Dobrin et al. | |
| 2003/0181120 A1 * | 9/2003 | Wu et al. | 442/394 |
| 2004/0038085 A1 | 2/2004 | Litton et al. | |
| 2004/0087235 A1 * | 5/2004 | Morman et al. | 442/394 |
| 2004/0118505 A1 | 6/2004 | Shimakawa et al. | |

FOREIGN PATENT DOCUMENTS

| | | | |
|---|---|---|---|
| EP | 0 090 380 | | 10/1983 |
| EP | 0 276 100 | | 7/1988 |
| EP | 0 333 212 | | 9/1989 |
| EP | 0 370 835 | | 5/1990 |
| EP | 0 379 763 | | 8/1990 |
| EP | 0 409 315 | | 1/1991 |
| EP | 0 551 327 | | 7/1993 |
| EP | 0 573 586 | | 12/1993 |
| EP | 0 575 509 | | 12/1993 |
| EP | 0 582 286 | | 2/1994 |
| EP | 0 712 304 | | 5/1996 |
| EP | 0 765 146 | | 4/1997 |
| EP | 0 782 639 | | 7/1997 |
| EP | 0 803 602 A1 | | 10/1997 |
| EP | 0 829 566 | | 3/1998 |
| EP | 0 852 483 | | 7/1998 |
| EP | 0 927 096 | | 7/1999 |
| EP | 1 066 962 | | 1/2001 |
| EP | 1 151 846 | | 11/2001 |
| GB | 1 521 579 | | 8/1978 |
| GB | 1 526 722 | | 9/1978 |
| GB | 1 526 723 | | 9/1978 |
| GB | 1 526 724 | | 9/1978 |
| GB | 1 553 102 | | 9/1979 |
| GB | 1 579 718 | | 11/1980 |
| GB | 1 598 737 | | 9/1981 |
| GB | 1 598 738 | | 9/1981 |
| WO | WO 92/16371 | | 10/1992 |
| WO | WO 95/16425 | | 6/1995 |
| WO | WO 96/10481 | | 4/1996 |
| WO | WO 96/16216 | | 5/1996 |
| WO | WO 98/04397 | | 2/1998 |
| WO | WO 99/42068 | | 8/1999 |
| WO | WO 00/19950 | | 4/2000 |
| WO | WO 00/23255 | | 4/2000 |
| WO | WO 00/23509 | | 4/2000 |
| WO | WO 0046023 | * | 8/2000 |
| WO | WO 00/56522 | | 9/2000 |
| WO | WO 00/69383 | | 11/2000 |
| WO | WO 01/15645 A1 | * | 3/2001 |
| WO | WO 01/23180 | | 4/2001 |
| WO | WO 01/54900 A1 | | 8/2001 |
| WO | WO 01/88245 | | 11/2001 |
| WO | WO 02/102592 | | 12/2002 |

* cited by examiner

EXTENSIBLE LAMINATE HAVING IMPROVED STRETCH PROPERTIES AND METHOD FOR MAKING SAME

FIELD OF INVENTION

The present invention relates to an extensible laminate having improved stretch properties and a method for making the extensible laminate. The improved stretch properties are achieved by mechanically stretching a laminate of an extensible nonwoven web and an elastic film in a cross direction.

BACKGROUND OF THE INVENTION

Composites of elastic and non-elastic material have been made by bonding the elastic material to the non-elastic material in a manner that allows the entire composite to stretch or elongate. Often these composites are used in garment materials, pads, diapers adult incontinence products, feminine hygiene products and the like. One such composite or laminate includes an extensible nonwoven material bonded to an elastomeric sheet.

However, such laminates make inefficient use of the elastic resins that are included in the elastomeric sheet. Generally, hysteresis and elasticity are inversely related. In other words, if a material has a higher hysteresis value it will be less elastic and if the material has a lower hysteresis value it is more elastic. Films made from the resins and compounds typically chosen for use in these laminates have a hysteresis value between about 25 percent and about 50 percent as measured using a 100% cycle test. In contrast, laminates made with these same films typically have hysteresis values between about 50 percent and about 75 percent as measured using a 100% cycle test. This is likely due to the interactions between the extensible nonwoven material and the elastomeric sheet, which is dependent on the level of attachment between the layers of the laminate.

Generally, the more attachment there is between the extensible nonwoven material and the elastomeric sheet, in terms of the number of bonds and/or the intensity or strength of the bonds, the worse the elastic properties of the laminate. Ideally, the attachments between the extensible nonwoven material and the elastomeric sheet should be sufficient to keep the layers of the laminate together but not unduly affect the elastic properties of the laminate.

When an extensible nonwoven web is laminated to an elastomeric sheet at least two types of bonds are typically formed between the webs: primary bonds and secondary bonds. Primary bonds are intentionally formed, are stronger and work to maintain the internal cohesion of the laminate such that when the laminate is stretched or elongated the layers do not separate from each other. Secondary bonds, on the other hand, are weaker and can be broken to a large extent during a first extension/relaxation cycle. As a result of the formation of these secondary bonds, the laminate is less elastic and more difficult to stretch particularly the first time the laminate is stretched. Generally, it is believed that the first stretch of the laminate causes the filaments of the extensible nonwoven material in the secondary bonds to cut through and/or detach from the elastomeric sheet. The required energy to cut through and/or detach these bonds is, in general, non-recoverable. Non-recoverable energy causes an energy loss or an increase in hysteresis.

Additionally, unstretched elastomeric sheets typically have poorer stretch properties during the first elongation/retraction cycle because the molecules making up the sheet are relatively non-uniformly or randomly oriented within the sheet. The required energy to orient the molecules, like that required to detach the secondary bonds, is, in general, non-recoverable and can also contribute to an increase in hysteresis.

In most instances, these laminates are included in consumer products without having been previously stretched. Thus, when a consumer uses a product including such a laminate they must exert more force to extend or elongate the laminate in order to achieve proper fit and comfort. Also, because the laminate has not been previously stretched it may stretch unevenly or discontinuously, especially if a non-uniform force is applied. This results in discomfort to the wearer and poor fit of the product as well as poor subsequent stretching of the laminate while in use.

With the foregoing in mind, there is a need or desire for an extensible laminate that makes efficient use of the stretch properties of the elastic film component. There is also a need or desire for an extensible laminate that a consumer may easily and uniformly stretch to provide better fit and more comfortable wear of a consumer product including the extensible laminate.

It is a feature and advantage of the invention to provide an extensible laminate that may be utilized in a consumer product to provide better fit and comfort. It is also a feature and advantage of the invention to provide a method for making an extensible laminate having improved stretch properties.

SUMMARY OF THE INVENTION

The present invention is directed to an extensible laminate having improved stretch properties such as reduced set and hysteresis. A method for making the extensible laminate is also disclosed.

In one embodiment, an extensible laminate includes an extensible nonwoven web laminated to an elastomeric sheet, wherein, after lamination, the extensible nonwoven web and the elastomeric sheet have been mechanically stretched in the cross direction by at least about 50 percent. The extensible laminate has a hysteresis value, measured during a first 100 percent elongation/retraction cycle, at least about 15 percent lower than a comparable unstretched extensible laminate. In another aspect, the extensible laminate has a lower set, measured during a first 100 percent elongation/retraction cycle, than a comparable unstretched extensible laminate. In a further aspect, the extensible laminate has a lower elongation/retraction ratio than a comparable unstretched extensible laminate.

A method for making an extensible laminate includes laminating an extensible nonwoven web to an elastomeric sheet to form a laminate and mechanically stretching the laminate in a cross direction by at least about 50 percent. The resulting extensible laminate has a lower hysteresis value, set and elongation/retraction ratio, than a comparable laminate that has not been mechanically stretched in the cross direction.

BRIEF DESCRIPTION OF THE DRAWINGS

These and other objects and features of this invention will be better understood from the following detailed description taken in conjunction with the drawings, wherein.

DEFINITIONS

Figure 1:
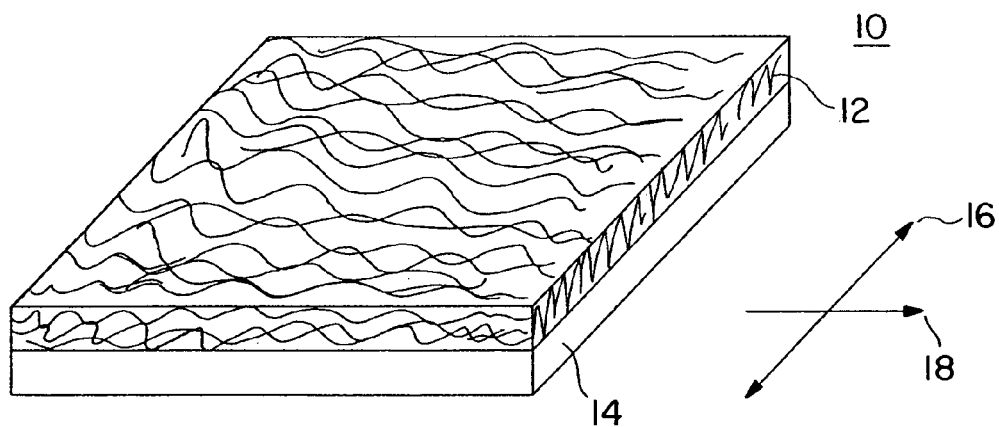
FIG. 1 is a plan view of an extensible laminate.

The term "extensible" refers to a material that can be stretched without breaking by at least 50% (to at least 150% of its initial unstretched length) in at least one direction, suitably by at least 100% (to at least 200% of its initial unstretched length). For example, an extensible material having an initial unstretched length of 3 inches (7.6 centimeters) may be stretched without breaking to at stretched length of at least 4.5 inches (11.4 centimeters) in at least one direction. The term includes elastic materials as well as materials that stretch but do not significantly retract such as, for example, necked nonwoven materials and inherently extensible nonwoven materials like bonded carded webs.

The terms "elastomeric" or "elastic" refer to a material that can be stretched without breaking by at least 50% (to least 150% of its initial unstretched length) in at least one direction and which, upon release of a stretching, biasing force, will recover at least 30% of its elongation within about one minute.

The term "biaxially extensible" refers to a material that may be stretched by at least about 50% in two directions perpendicular to each other (e.g. stretchable in a machine direction and cross direction, or in a longitudinal direction, front to back, and a lateral direction, side to side). The term includes biaxially extensible laminates such as those disclosed in, for example, U.S. Pat. Nos. 5,114,781 and 5,116,662 to Morman, which are incorporated by reference.

The term "inelastic" refers to both materials that do not stretch by 50% or more and to materials that stretch by that amount but do not retract by more than 30%. Inelastic materials also include materials that do not extend, e.g., which tear when exposed to a stretching force.

The term "machine direction" for a nonwoven web, film or laminate refers to the direction in which it was produced. The term "cross direction" for a nonwoven web, film or laminate refers to the direction perpendicular to the machine direction. Dimensions measured in the cross direction are referred to as "width" dimension, while dimensions measured in the machine direction are referred to as "length" dimensions.

The term "cycling test" or "100% cycling test" refers to a method for determining the elastic properties of an extensible laminate. Further details regarding the cycling test are disclosed below in the section entitled "TEST FOR DETERMINING HYSTERESIS, SET AND ELONGATION/RETRACTION RATIO"

The term "hysteresis" or "hysteresis value" refers to an elastic property of a material determined using the cycling test disclosed below. Hysteresis is expressed as the percentage of energy recovered upon retraction of an elongated material.

The term "set" refers to an elastic property of a material determined using the cycling test disclosed below. Set is expressed as the percentage of the amount of retraction of a material from the point of maximum extension to the point at which the retraction force first measures 10 grams or lower divided by the maximum extension length.

The term "elongation/retraction ratio" or "E/R ratio" refers to an elastic property of a material determined using the cycling test disclosed below. The E/R ratio is expressed as a ratio of extension force per retraction force.

The term "polymer" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and atactic symmetries.

As used herein, the term "single-site catalyzed" refers to polyolefins produced by metallocene-catalyzed polymerization reactions and/or constrained geometry-catalyzed polymerization reactions. Such catalysts are reported in "Metallocene Catalysts Initiate New Era in Polymer Synthesis", Ann M. Thayer, Chemical & Engineering News, Sept. 11, 1995, p. 15.

As used herein, the term "sheet" refers to a generally flat structure, which can be composed of a nonwoven material or web, a woven structure, a scrim, a film or a foam. The sheet may include an elastomeric material.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spundbonding processes, air laying processes, coforming processes, and bonded carded web processes. The basis weight of nonwoven fabrics or webs is usually expressed in ounces of material per square yard (osy) or grams of material per square meter (gsm) and the fiber diameters used are usually expressed in microns. (Note that to convert from osy to gsm, multiply osy by 33.91).

The term "microfibers" means small diameter fibers typically having an average fiber denier of about 0.005 to 50. Fiber denier is defined as grams per 9000 meters of fiber. For a fiber having a circular cross-section, denier may be calculated as fiber diameter in microns squared, multiplied by the density in grams per cubic centimeter (g/cc) multiplied by 0.00707. For fibers made of the same polymer, a lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying that result by 0.00707. Thus, a 15 micron polypropylene has a denier of about 1.42 calculated as ($15^2 \times 0.89 \times 0.00707 = 1.415$). Outside the United States the unit of measurement is more commonly the "tex" which is defined as grams per kilometer of fiber. Tex may be calculated as denier/9.

As used herein, the term "interfiber bonding" means bonding produced by thermal bonding or entanglement between the individual nonwoven fibers to form a coherent web structure. Fiber entangling is inherent in the meltblown process but may be generated or increased by processes such as, for example, hydraulic entangling or needlepunching. One or more thermal bonding steps are employed in most processes for forming spunbond webs. Alternatively and/or additionally, a bonding agent can be utilized to increase the desired bonding and to maintain structural coherency of the web. For example, powdered bonding agents and chemical solvent bonding may be used.

The term "spunbond fibers" refers to small diameter fibers which are formed by extruding molten thermoplastic material as filaments from a plurality of fine capillaries of a spinneret having a circular or other configuration, with the diameter of the extruded filaments then being rapidly reduced as in, for example, U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers can be microfibers that may be continuous, are generally smaller than about 1.0 denier, and are generally self-bonding when deposited onto a collecting surface. Meltblown macrofibers, which can be in excess of 60 denier, can also be produced.

"Bonded carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales which are placed in an opener/blender or picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well known bonding method, particularly when using bicomponent staple fibers, is through-air bonding.

As used herein, the term "inherently extensible nonwoven material" refers to a nonwoven material that may be readily stretched by at least 50% in at least one direction without further processing such as necking or creping.

The term "neck" or "neck stretch" interchangeably mean that the fabric, nonwoven web or laminate is drawn such that it is extended under conditions reducing its width or its transverse dimension by stretching lengthwise or increasing the length of the fabric. The controlled drawing may take place under cool temperatures, room temperature or greater temperatures and is limited to an increase in the overall dimension in the direction being drawn up to the elongation required to break the fabric, nonwoven web or laminate, which in most cases is about 1.2 to about 1.6 times. When relaxed, the fabric, nonwoven web or laminate does not return totally to its original dimensions. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric.

The term "neckable material" or "neckable layer" means any material or layer which can be necked such as a nonwoven, woven, or knitted material, or laminate containing one of them. As used herein, the term "necked material" refers to any material which has been drawn in at least one dimension, (e.g., lengthwise), reducing the transverse dimension, (e.g., width), such that when the drawing force is removed, the material can be pulled back to its original width. The necked material generally has a higher basis weight per unit area than the un-necked material. When the necked material is pulled back to its original width, it should have about the same basis weight as the un-necked material. This differs from stretching/orienting the film layer, during which the film is thinned and the basis weight is reduced. Suitable nonwoven webs for use in the invention are made from inelastic polymer(s).

As used herein, the term "reversibly necked material" refers to a necked material that has been treated while necked to impart memory to the material so that, when a force is applied to extend the material to its pre-necked dimensions, the necked and treated portions will generally recover to their necked dimensions upon termination of the force. One form of treatment is the application of heat. Generally speaking, extension of the reversibly necked material is substantially limited to extension to its pre-necked dimensions. Therefore, unless the material is elastic, extension too far beyond its pre-necked dimensions will result in material failure. A reversibly necked material may include more than one layer, for example, multiple layers of spunbond web, multiple layers of meltblown web, multiple layers of bonded carded web or any other suitable combination or mixtures thereof, as described in U.S. Pat. No. 4,965,122 to Morman, which is incorporated by reference.

The term "percent neckdown" refers to the ratio determined by measuring the difference between the un-necked dimension (width) and the necked dimension (width) of the neckable material and then dividing that difference by the un-necked dimension of the neckable material.

As used herein, the terms "elastomeric sheet" and "elastomeric web" refer to: elastomeric films formed by extrusion, casting or other methods known in the art; elastomeric nonwoven fabrics such as, for example, meltblown elastomeric webs as disclosed in U.S. Pat. No. 4,663,220 to Wisneski et al., which is incorporated by reference; elastomeric foams; elastomeric scrim webs; and elastomeric filament webs.

The term "film" refers to a thermoplastic film made using a film extrusion process, such as a cast film or blown film extrusion process. This term includes films rendered microporous by mixing a polymer with filler, forming a film from the mixture, and stretching the film.

The term "breathable" refers to a material which is permeable to water vapor as measured by the water vapor transmission test, having a water vapor transmission rate (WVTR) of at least about 300 g/m$^2$/24 hours. The water vapor transmission test is disclosed in U.S. Pat. No. 5,955,187 issued to McCormack et al., which is hereby incorporated by reference in a manner consistent herewith.

The term "co-extrusion" or "co-extruded" refers to films including two or more layers of thermoplastic material that are extruded simultaneously to form a single, integrated sheet of film without the need for a further attachment or lamination process to bond the layers together.

As used herein, the term "extensible laminate" refers to a material having an elastomeric sheet joined to an extensible material at least at two places (e.g., a single-faced extensible laminate). The elastomeric sheet may be joined to the extensible material at intermittent points or may be completely bonded thereto. The joining is accomplished while the elastomeric sheet and the extensible material are in juxtaposed configuration. An extensible laminate may include more than two layers. For example, the elastomeric sheet may have an extensible material joined to both of its sides so that a three-layer extensible laminate is formed having a structure of extensible material/elastomeric sheet/ extensible material (e.g., a two-faced extensible laminate). Additional elastic or elastomeric sheets, necked material layers, and/or inherently extensible materials such as bonded carded webs may be added. Other combinations of elastomeric sheets and extensible materials may be used, for instance, as indicated in commonly assigned U.S. Pat. Nos. 5,114,781 and 5,116,662 to Morman and U.S. Pat. No. 5,336,545 to Morman et al., which are hereby incorporated by reference.

The term "comparable unstretched extensible laminate" refers to an extensible laminate including the same extensible nonwoven material or materials and the same elastomeric sheet or sheets formed by the same process that has not been mechanically stretched in the cross-direction by at least about the same amount as an extensible laminate of the present invention.

The term "garment" includes pant-like absorbent garments and medical and industrial protective garments. The term "pant-like absorbent garment" includes without limitation diapers, training pants, swim wear, absorbent underpants, baby wipes, adult incontinence products, and feminine hygiene products.

The term "medical protective garment" includes without limitation surgical garments, gowns, aprons, facemasks, and drapes. The term "industrial protective garment" includes without limitation protective uniforms and workwear.

As used herein, the term "tenter frame" refers to a machine or apparatus used to stretch a material to a specified width. A typical machine includes a pair of endless chains on horizontal tracks. The material is firmly held at the edges by pins or clips on the two chains that diverge as they advance thereby adjusting the material to the desired width.

As used herein, the term "comprising" opens the claim to inclusion of additional materials or process steps other than those recited.

These terms may be defined with additional language in the remaining portions of the specification.

DESCRIPTION OF PREFERRED EMBODIMENTS

The present invention provides an extensible laminate having improved stretch properties. The improved stretch properties are achieved without a change in the raw materials typically used to make the laminate. A laminate of an extensible nonwoven web and an elastomeric sheet is mechanically stretched in a cross direction by at least about 50 percent, suitably by at least about 65 percent, desirably by at least about 75 percent, and in one embodiment by at least about 100 percent. The resulting extensible laminate has a hysteresis value and set that are lower than a hysteresis value and set for a comparable laminate that has not been mechanically stretched in the cross direction. The resulting laminate also has a lower elongation/retraction ratio than a comparable unstretched laminate. Also provided is a method of making the extensible laminate.

Generally, the extensible laminate should have a hysteresis value, measured during a first 100 percent elongation/retraction cycle, at least about 15 percent lower than a comparable unstretched extensible laminate, desirably at least about 20 percent lower, and in one embodiment at least about 25 percent lower. Suitably, the extensible laminate should have a set, measured during a first 100 percent elongation/retraction cycle, at least about 10 percent lower than a comparable unstretched extensible laminate, more suitably at least about 20 percent lower, and in one embodiment at least about 30 percent lower. Additionally, the extensible laminate should have an elongation/retraction ratio (E/R ratio) at least about 15 percent lower than a comparable unstretched extensible laminate, desirably at least about 20 percent lower, and in one embodiment at least about 25 percent lower. The reduced hysteresis value, set and E/R ratio should be relatively permanent. By "relatively permanent" we mean that an extensible laminate tested 7 days after cross-directional stretching should have: a hysteresis value, measured during a first 100 percent elongation/retraction cycle, at least about 15 percent lower than a comparable unstretched extensible laminate, desirably at least about 20 percent lower; a set, measured during a first 100 percent elongation/retraction cycle, at least about 10 percent lower than a comparable unstretched extensible laminate, suitably at least about 20 percent lower; and an E/R ratio at least about 15 percent lower than a comparable unstretched extensible laminate, suitably at least about 20 percent lower. Furthermore, an extensible laminate tested 30 days after cross-directional stretching should have: a hysteresis value, measured during a first 100 percent elongation/retraction cycle, at least about 15 percent lower than a comparable unstretched extensible laminate, desirably at least about 20 percent lower; a set, measured during a first 100 percent elongation/retraction cycle, at least about 10 percent lower than a comparable unstretched extensible laminate, suitably at least about 20 percent lower; and an E/R ratio at least about 15 percent lower than a comparable unstretched extensible laminate, suitably at least about 20 percent lower. The extensible laminate is suitable for use in a variety of consumer products including, but not limited to, absorbent garments, diapers, training pants, swimwear, adult incontinence products, feminine hygiene products, and medical or industrial protective garments.

As shown in FIG. 1, an extensible laminate 10 includes an extensible nonwoven web 12 laminated to an elastomeric sheet 14. The extensible laminate 10 is extendable in a cross direction 16 due to the influence of the extensible nonwoven web 12. When a cross-direction extension force is removed the laminate 10 will return substantially to its manufactured configuration due to the influence of the elastomeric sheet 14.

Optionally, the extensible laminate 10 may include additional layers of nonwoven material and/or elastomeric material. For example, the extensible laminate may include first and second extensible nonwoven webs laminated to either side of an elastomeric sheet. Alternatively, the extensible laminate 10 may include first and second elastomeric sheets laminated to each other and/or an extensible nonwoven web.

Figure 2A:
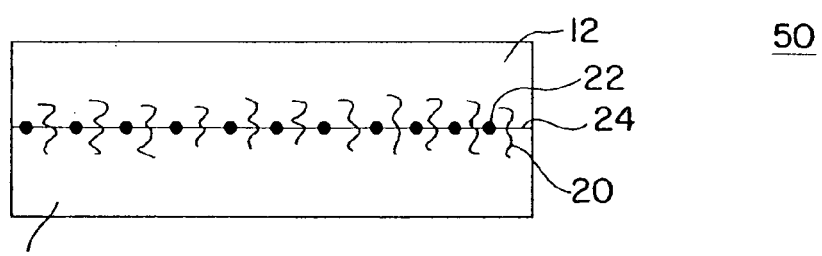
FIGS. 2a and 2b are cross-sectional views of a laminate.
Figure 2B:
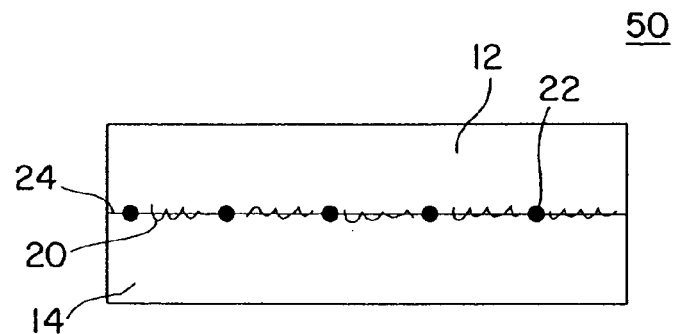

Generally, during the lamination process two types of bonds are formed between the extensible nonwoven web 12 and the elastomeric sheet 14. Referring to FIGS. 2a and 2b, a laminate 50 includes primary bonds 20 and secondary bonds 22 that attach the extensible nonwoven web 12 to the elastomeric sheet 14.

In one aspect, referring to FIG. 2a, the primary bonds 20 may involve bonding across an interfacial plane 24 between the extensible nonwoven web 12 and the elastomeric sheet 14 wherein portions of the two materials become entangled with and/or encapsulated within each other such as occurs during point-bond lamination techniques. As a result, the primary bonds 20 are resistant to breakage during elongation or extension of the laminate 50 thereby imparting internal cohesion to the laminate 50. Thus, the extensible nonwoven web 12 does not easily separate from the elastomeric sheet 14 during extension or elongation.

In another aspect, referring to FIG. 2b, the primary bonds 20 may involve bonding along the interfacial 24 wherein the bond intensity or strength of the bonds is greater such as may occur during thermal calender lamination techniques. As a result the primary bonds 20 are resistant to breakage during elongation or extension of the 50 thereby imparting internal cohesion to the laminate 50. Thus, the extensible nonwoven web 12 does not easily separate from the elastomeric sheet 14 during extension or elongation.

The best elastic properties for the extensible laminate 10 are attained when the elastomeric sheet 14 and the extensible nonwoven web 12 stretch totally independently of each other (e.g. when there is no physical attachment between the elastomeric sheet 14 and the extensible nonwoven web 12). However, some physical attachment is obviously required to form the laminate. Adequate attachment is purposely formed (primary bonds) to ensure that the laminate has adequate internal cohesion but often some unnecessary attachment (secondary bonds) also occurs. These secondary bonds, which are not required for acceptable laminate formation, negatively impact the laminate elastic properties.

The secondary bonds 22, which typically form on the interfacial plane 24, generally do not involve significant entanglement or encapsulation of the extensible nonwoven web 12 and the elastomeric sheet 14. Additionally, such secondary bonds typically have a lower bond strength or intensity. As a result secondary bonds 22 are generally weaker than primary bonds 20. However, it is believed that the secondary bonds 22 are detrimental to the elastic properties of the laminate 50. The secondary bonds 22, although not strong enough to impart significant internal cohesion to the laminate, do make the laminate stiffer and less elastic. Generally, such laminates have a hysteresis value, measured during a first 100 percent elongation/retraction cycle, greater than about 45 percent, often between about 50 percent and about 75 percent. Additionally, such laminates typically have a set, measured during a first 100 percent elongation/retraction cycle, of 9 percent or greater. As a result, when the laminate 50 is stretched in the cross direction for the first time, a greater amount of force must be used to achieve maximum stretch and to achieve proper fit when a laminates 50 is used in a consumer product. Additionally, the higher set may cause product bagging and poor fit.

Suitably, the extensible nonwoven web 12 may be an inherently extensible nonwoven material such as, for example, a crimped bicomponent spunbond material as disclosed in commonly assigned U.S. Pat. No. 5,418,045 to Pike et al., which is hereby incorporated by reference, or an oriented bonded carded web.

Other suitable extensible nonwoven materials include biaxially extensible nonwoven materials such as neck stretched/creped spunbond. The machine direction and cross direction extensible nonwoven material can be provided by stretching a fibrous nonwoven web in a machine direction to cause necking (and extensibility) in the cross direction. Alternatively, the nonwoven material may be a very loose collection of fibers bonded discontinuously in the cross direction such that the material can be stretched in the cross direction. The same material with the imparted cross direction extensibility may be crimped or creped in the machine direction to cause machine direction extensibility.

The extensible nonwoven material 12 may also be a necked nonwoven material such as, for example, a necked spunbonded web, a necked meltblown web or a necked bonded carded web. Suitably, the necked nonwoven material may have a percent neckdown of from about 20 percent to about 75 percent. Desirably, the necked nonwoven web may have a percent neckdown of from about 30 percent to about 70 percent.

If the necked nonwoven material is a web of meltblown fibers, it may include meltblown microfibers. The necked nonwoven material may be made from any material that can be necked by tension and extended, upon application of a force to extend the necked material, to its pre-necked dimensions. Certain polymers such as, for example, polyolefins, polyesters and polyamides may be heat treated under suitable conditions to impart such memory. Exemplary polyolefins include one or more of polyethylene, polypropylene, polybutene, ethylene copolymers, propylene copolymers and butene copolymers. Polypropylenes that have been found useful include, for example, polypropylene available from the Himont Corporation of Wilmington, Del. under the trade designation PF-304, polypropylene available from the Exxon-Mobil Chemical Company of Baytown, Tex. under the registered trademark ESCORENE PD-3445, and polypropylene available from the Shell Chemical Company of Houston, Tex. under the trade designation DX 5A09. Polyethylenes may also be used, including ASPUN 6811A and 2553 linear low density polyethylenes from the Dow Chemical Company of Midland, Mich., as well as various high density polyethylenes. Chemical characteristics of these materials are available from their respective manufacturers.

In one embodiment of the present invention, the extensible nonwoven web 12 may be a multilayer material having, for example, at least one layer of spunbonded web joined to at least one layer of meltblown web, bonded carded web or other suitable material. For example, the extensible nonwoven web 12 may be a multilayer material having a first layer of spunbonded polyolefin having a basis weight from about 0.2 to about 8 ounces per square yard (osy) (about 6.8 to about 271.3 grams per meter (gsm)), a layer of meltblown polyolefin having a basis weight from about 0.1 to about 4 osy (about 3.4 to about 113.4 gsm), and a second layer of spunbonded polyolefin having a basis weight of about 0.2 to about 8 osy (about 6.8 to about 271.3 gsm).

Alternatively, the extensible nonwoven web 12 may be single layer of material such as, for example, a spunbonded web having a basis weight of from about 0.2 to about 10 osy (about 6.8 to about 339.1 gsm) or a meltblown web having a basis weight of from about 0.2 to about 8 osy (about 6.8 to about 271.3 gsm).

The extensible nonwoven web 12 may also include a composite material made of a mixture of two or more different fibers or a mixture of fibers and particulates. Such mixtures may be formed by adding fibers and/or particulates to a gas stream in which meltblown fibers are carried so that an intimate entangled commingling of meltblown fibers and other materials (e.g., wood pulp, staple fibers or particulates such as, for example, superabsorbent materials) occurs prior to collection of the fibers upon a collecting device to form a coherent web of randomly dispersed meltblown fibers and other materials such as disclosed in U.S. Pat. No. 4,100,324 to Anderson et al., which is incorporated by reference.

The fibers of the extensible nonwoven web 12 should be joined by interfiber bonding using one or more of the bonding processes described in the foregoing "DEFINITION" of interfiber bonding.

The elastomeric sheet 14 may be made from any material that may be manufactured in sheet form. For example, the elastomeric sheet 14 may be an elastomeric nonwoven web, an elastomeric foam, an elastomeric scrim web, or an elastomeric filament web. A nonwoven elastomeric web may be formed by meltblowing a suitable resin or blends containing the same to provide a nonwoven elastomeric web. A specific example of a nonwoven elastomeric web is disclosed in U.S. Pat. No. 4,663,220 to Wisneski et al., which is hereby incorporated by reference.

Alternatively, the elastomeric sheet 14 may be an elastomeric film made from a styrene copolymer, for example, a polymer selected from styrene-butadiene-styrene, styrene-isoprene-styrene, styrene-ethylene/butylene-styrene, styrene-ethylene/propylene-styrene, and combinations thereof. Such styrene copolymers are typically highly elastic and substantially control the overall elasticity of the co-extruded elastomeric film. Styrene copolymers suitable for use in the present invention are available from Kraton Polymers of Houston, Tex. the under the registered trademark KRATON. One such copolymer may be, for example, KRATON G-1657. Suitable elastomeric blends containing KRATON copolymers include, for example, KRATON G-2755 and KRATON G-2760.

Other exemplary materials which may be used include polyurethane elastomeric materials such as, for example, those available under the registered trademark ESTANE from Noveon, Inc. of Cleveland, Ohio, polyamide elastomeric materials such as, for example, those available under the registered trademark PEBAX from Atofina Chemical Company of Philadelphia, Penn., and polyester elastomeric materials such as, for example, those available under the registered trademark HYTREL from E.I. duPont De Nemours & Company of Wilmington, Del. Formation of elastomeric sheets from polyester elastic materials is disclosed in, for example, U.S. Pat. No. 4,741,949 to Morman et al., hereby incorporated by reference.

The elastomeric film may include a single-site catalyzed copolymer such as "metallocene" polymer produced according to a metallocene process. The term "single-site catalyzed" as used herein includes those polymer materials that are produced by the polymerization of at least ethylene using metallocenes or constrained geometry catalysts, a class of organometallic complexes, as catalysts. For example, a common metallocene is ferrocene, a complex of a metal between two cyclopentadienyl (Cp) ligands. Metallocene process catalysts include bis (n-butylcyclopentadienyl) titanium dichloride, bis(n-butylcyclopentadienyl) zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-fluorenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to Dow Chemical Company of Midland, Mich. Such compounds are also discussed in U.S. Pat. No. 5,064,802 to Stevens et al., also assigned to Dow.

Desirably, the single-site catalyzed ethylene-alpha olefin copolymers have a density of about 0.860 to about 0.900 grams per cubic centimeter and are selected from copolymers of ethylene and 1-butene, copolymers of ethylene and 1-hexene, copolymers of ethylene and 1-octene and combinations thereof. Such single-site catalyzed ethylene-alpha olefin copolymers are available from Exxon-Mobil Chemical Company of Baytown, Tex. under the registered trademarks EXXPOL for polypropylene based polymers and EXACT for polyethylene based polymers. DuPont Dow Elastomers, L.L.C. of Wilmington, Del. has polymers commercially available under the registered trademark ENGAGE. Single-site catalyzed ethylene-alpha olefin copolymers are also available under the registered trademark AFFINITY from Dow Chemical Company of Midland, Mich. Suitable single-site catalyzed ethylene-alpha olefin copolymers for use in the present invention include, for example, ENGAGE EG8200 and AFFINITY XUS58380.01L.

Elastomeric polymers including polypropylene, alone or in combination with other elastomeric polymers or less elastic materials, are also suitable for forming the elastomeric film. For example, the elastomeric film may be formed from an elastomeric homopolymer of polypropylene, an elastomeric copolymer of polypropylene, or a combination thereof.

A polyolefin may be used alone to form an extensible film or may be blended with an elastomeric polymer to improve the processability of the film composition. The polyolefin may be one which, when subjected to an appropriate combination of elevated temperature and elevated pressure conditions, is extrudable, alone or in blended form. Useful polyolefin materials include, for example, polyethylene, polypropylene and polybutene, including ethylene copolymers, propylene copolymers and butene copolymers. A particularly useful polyethylene may be obtained from U. S. I. Chemical Company under the registered trademark PETROTHENE NA601. Two or more of the polyolefins may be utilized. Extrudable blends of elastomeric polymers and polyolefins are disclosed in, for example, U.S. Pat. No. 4,663,220 to Wisneski et al., hereby incorporated by reference.

The elastomeric film may also be a multilayer material in that it may include two or more coherent webs or sheets. Additionally, the elastomeric sheet 14 may be a multilayer material in which one or more of the layers contain a mixture of elastic and extensible fibers or particulates. An example of the latter type of elastic web is disclosed in U.S. Pat. No. 4,209,563 to Sisson, herein incorporated by reference, in which elastomeric and extensible fibers are commingled to form a single coherent web of randomly dispersed fibers.

Exemplary elastomeric films for use in the present invention include blends of (poly/poly(ethylenebutylene)/polystyrene) block copolymers, metallocene-derived polymers and polyolefins. For example, the elastomeric film may be formed from a blend of from about 15 percent to about 75 percent of a metallocene-derived polyolefin, from about 10 percent to about 60 percent (polystyrene/poly(ethylenebutylene)/polystyrene) block copolymers, and from 0 to about 15 percent of a low density polyethylene.

In another aspect, the elastomeric sheet 14 may be an elastomeric foam material. One suitable elastomeric foam material is an elastomeric polyurethane foam.

The elastomeric sheet 14 may include a filled elastomeric film. The filled elastomeric film may be formed by blending one or more polyolefins and/or elastomeric resins with a particulate filler. The filler particles may include any suitable organic or inorganic material. Generally, the filler particles should have a mean particle diameter of about 0.1 to about 8.0 microns, desirably about 0.5 to about 5.0 microns, and more desirably about 0.8 to about 2.0 microns. Suitable inorganic filler particles include without limitation calcium carbonate, non-swellable clays, silica, alumina, barium sulfate, sodium carbonate, talc, magnesium sulfate, titanium dioxide, zeolites, aluminum sulfate, diatomaceous earth, magnesium carbonate, barium carbonate, kaolin, mica, carbon, calcium oxide, magnesium oxide, aluminum hydroxide. Suitable organic filler particles include polymer particles or beads. Calcium carbonate is the presently desired filler particle. The filled elastomeric sheet 14 may be stretch-thinned to cause void formation around the filler particles thereby making the film breathable.

The elastomeric sheet 14 may be formed by any number of conventionally known processes, including but not limited to, flat die extrusion, blown film (tubular) processes, casting, co-extrusion and the like. Suitably, the elastomeric sheet 14 may have a basis weight of about 5 to about 100 grams per square meter, desirably about 25 to about 60 grams per square meter.

Without being bound thereby, it is believed that the molecules in the elastomeric sheet 14 are predominantly oriented in the machine directions and thus the elastomeric sheet has its best elastic properties in the machine direction. The one time, cross-directional mechanical stretching of this invention orients some of the molecules in the cross direction, thus improving cross-directional elastic properties of the elastomeric sheet in subsequent stretches. It is theorized that during the lamination of an extensible nonwoven web 12 and an elastomeric sheet 14 mechanically stretching in a cross direction aids in breaking up microscopic domains within the elastomeric resin resulting in an extensible laminate 10 having improved stretch properties in subsequent elongation/retraction cycles.

Figure 3:
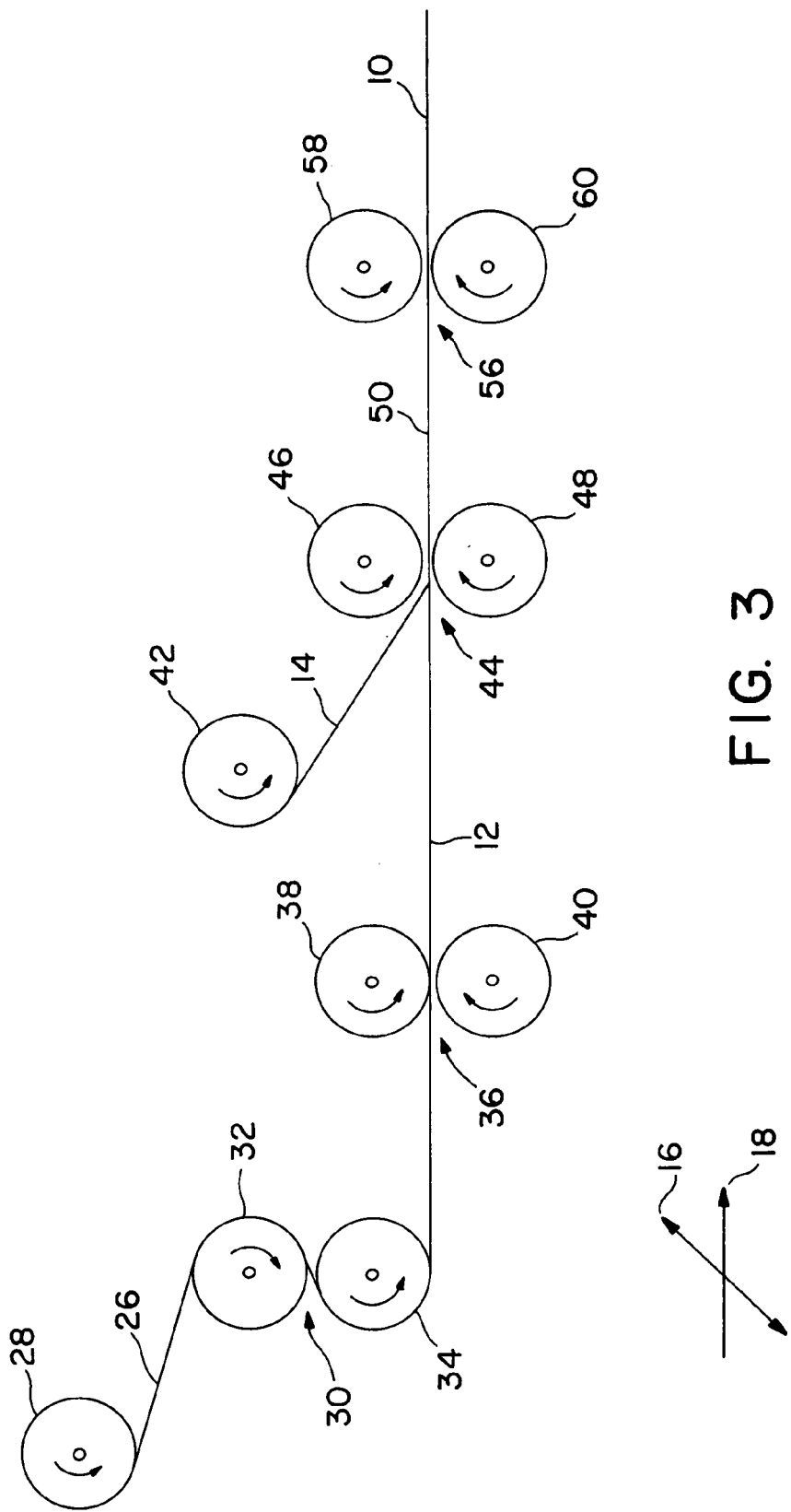
FIG. 3 is a schematic views of a process for making an extensible laminate utilizing grooved rolls to mechanically stretch a laminate in a cross direction.

FIG. 3 schematically illustrates a method for making an extensible laminate 10 of the invention including an extensible nonwoven web 12 and an elastomeric sheet 14. In this method a laminate 50 of the extensible nonwoven web 12 and the elastomeric sheet 14 is mechanically stretched in the cross-direction by at least about 50 percent, suitably by at least about 65 percent, desirably by at least about 75 percent, advantageously by at least about 100 percent. Mechanical stretching is preferred to ensure that a uniform force is applied across the laminate for a uniform amount of time. It is believed that mechanically stretching the laminate 50 in the cross direction results in an extensible laminate having improved and more consistent stretch properties, such as lower hysteresis and set, particularly in subsequent elongation/relaxation cycles.

Referring to FIG. 3, a method of making an extensible laminate 10 includes providing a nonwoven material web 26 on a supply roll 28. The nonwoven material web 26 passes through a first nip 30, including nip rolls 32 and 34, turning at a first surface velocity; and through a second nip 36, including nip rolls 38 and 40, turning at a second surface velocity that is higher than the first surface velocity thereby forming an extensible nonwoven web 12. Necking of the nonwoven material web 26 between the first nip 30 and the second nip 36 in a machine direction 18 is effected by the different surface velocities of the nip rolls. Suitably, the resulting necked nonwoven web 12 has a percent neckdown of about 20 to about 75 percent, desirably about 30 to about 70 percent.

Alternatively, the nonwoven material web 26 on supply roll 28 may be a pre-necked nonwoven material or an inherently extensible nonwoven material that may be laminated directly with an elastomeric sheet 14 without any prior inline processing.

An elastomeric sheet 14 is unrolled from a supply roll 42. The elastomeric sheet 14 and the extensible nonwoven web 12 are passed through a third nip 44, including nip rolls 46 and 48, to form a laminate 50.

Figure 4:
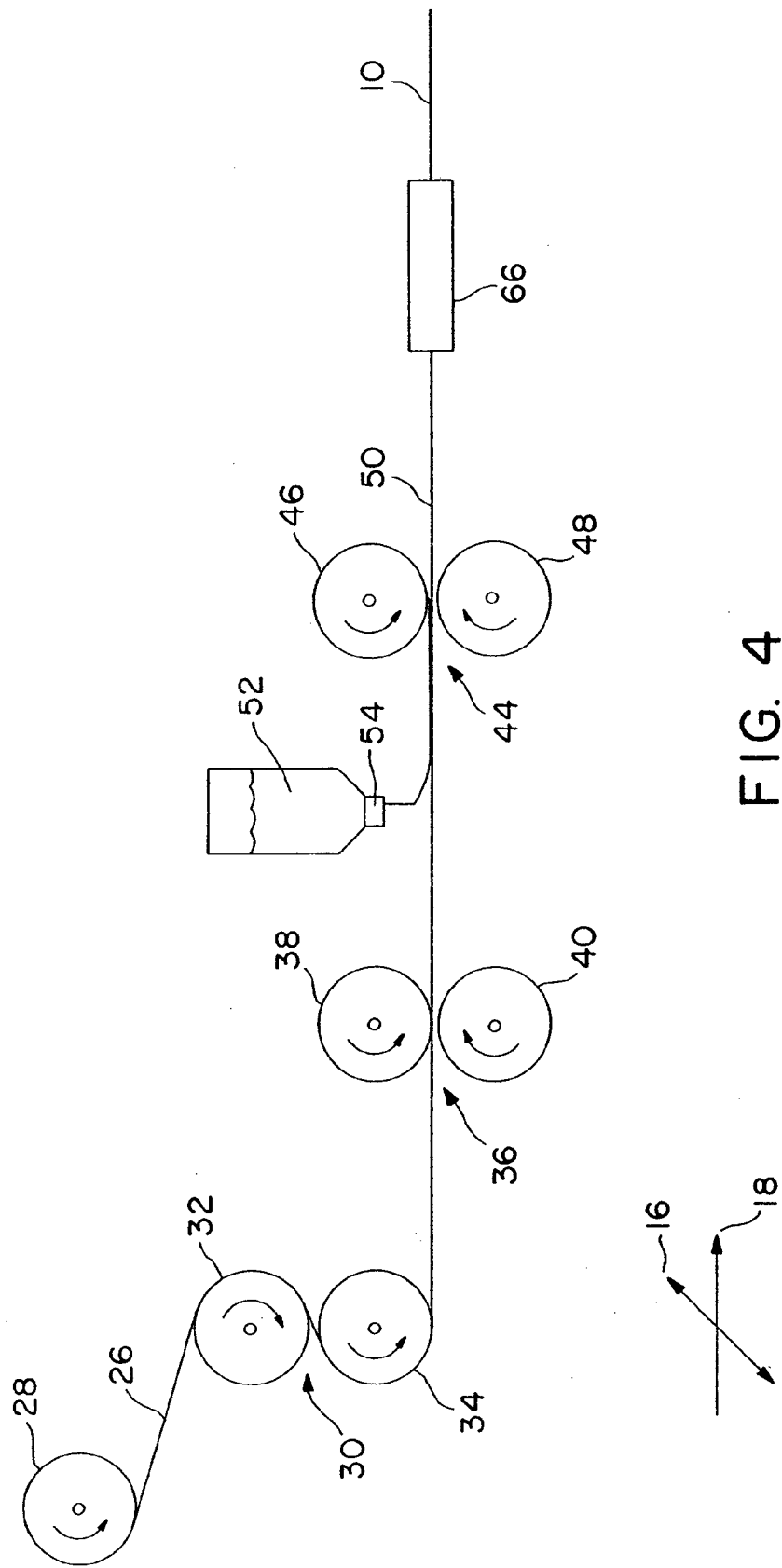
FIG. 4 is a schematic view of a process for making an extensible laminate utilizing a tenter frame to mechanically stretch a laminate in a cross direction.

Alternatively, as shown in FIG. 4, the elastomeric sheet 14 may be an elastomeric film formed by an extrusion process just prior to lamination to the extensible nonwoven web 12. A molten elastomer 52 is extruded through a die tip 54 to form an extruded elastomeric sheet 14. The extruded elastomeric sheet 14 is deposited directly onto the extensible nonwoven web 12 and the two layers are laminated together in the third nip 44. The extruded elastomeric sheet 14 may contact the extensible nonwoven web material 12 within about 0.1 to about 1.0 second after the film leaves the die tip 54, suitably within about 0.25 to about 0.5 seconds, desirably within about 0.3 and about 0.45 seconds. The elastomeric sheet 14 may be extruded at a temperature of about 180° C. to about 300° C., suitably of about 200° C. to about 250° C. Light pressure is applied in the third nip 44 to thermally bond the elastomeric sheet 14 (in a relatively untensioned state) to the tensioned necked nonwoven web 12. The nip rolls 46 and 48 may or may not be patterned, need not be heated, and may be chilled (e.g. to a temperature of about 10° C. to about 30° C.) so as to quench the elastomeric sheet 14 to the extensible nonwoven web 12.

The laminate 50 can be stretched in the cross direction 16 due to the extendability of the extensible nonwoven web 12. Upon relaxation, the laminate 50 may return substantially to its original manufactured configuration depending on the retractive force of the elastomeric sheet 14 and how retractive the elastomer is. Generally, the laminate 50 may have a hysteresis value greater than about 45 percent, typically greater than about 50 percent. The laminate 50 may have a hysteresis value as high as about 75 percent depending upon the degree of secondary bond formation during lamination and the number of microscopic domains existing within the elastomeric resin or resins that make up the film. Generally, the laminate 50 may have a set of 9 percent or greater.

The extensible nonwoven web 12 may be laminated to the elastomeric sheet 14 by a variety of processes including, but not limited to adhesive bonding, thermal bonding, point bonding, ultrasonic welding and combinations thereof. For example, nip rolls 46 and 48 may be heated to a temperature of about 93° C. to about 135° C. such that the extensible nonwoven web 12 is thermally bonded to the elastomeric sheet 14.

Figure 3A:
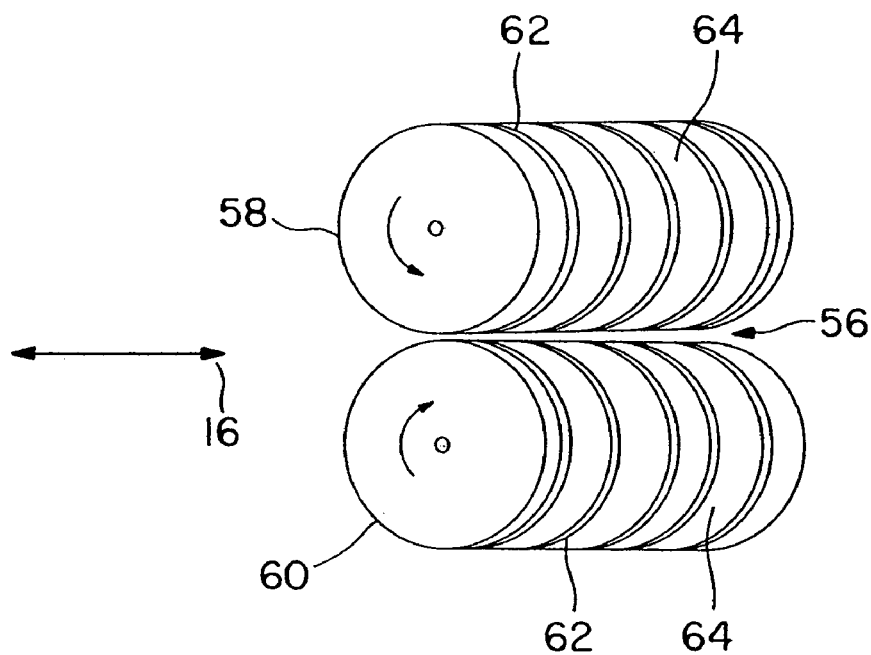
FIGS. 3*a* and 3*b* are close-up views of the grooved rolls utilized in the process shown in FIG. 3.
Figure 3B:
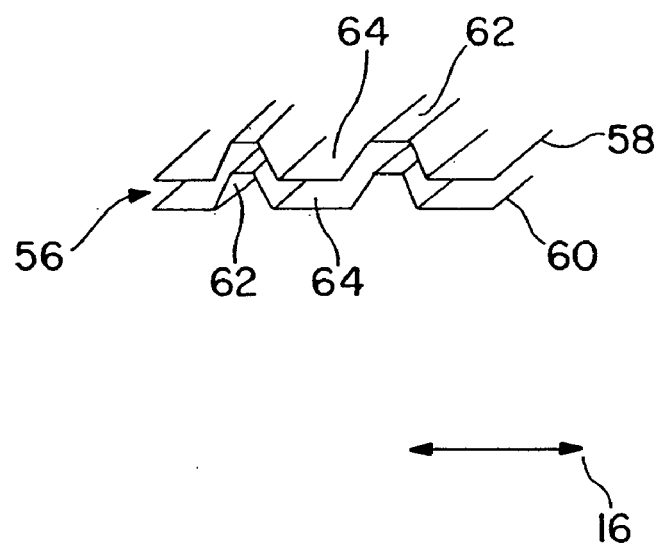

Referring again to FIG. 3, the laminate 50 is passed through a fourth nip 56, including grooved rolls 58 and 60, such that the laminate 50 is mechanically (incrementally) stretched in a cross direction 16 to produce an extensible laminate 10 having improved stretch properties. As shown in FIG. 3a, grooved rolls 58 and 60 include a plurality of ridges 62 defining a plurality of grooves 64 positioned across the grooved rolls 58 and 60 in the cross direction 16. Generally, the grooves 64 should be oriented perpendicular to the direction of stretch of the material. In other words, the grooves 64 should be oriented in the machine direction in order to stretch the laminate 50 in the cross-direction. Referring to FIG. 3b, the ridges 62 of grooved roll 58 intermesh with the grooves 64 of grooved roll 60 and the grooves 64 of grooved roll 58 intermesh with the ridges 62 of grooved roll 60 in the fourth nip 56 such that the laminate 50 is mechanically stretched in the cross direction 16. Suitably, the laminate 50 is mechanically stretched in the cross direction 16 by at least about 50 percent, desirably by at least about 65 percent, more desirably by at least about 75 percent, most desirably by about 100 percent. As the mechanically stretched laminate 50 exits the fourth nip 56 it is allowed to relax toward its substantially pre-necked dimension thereby forming the extensible laminate 10 of the present invention. The extensible laminate 10 may be wound onto a take-up roll (not shown) for later use in an offline process or may be transported to an inline process for incorporation into a consumer product.

Figure 4A:
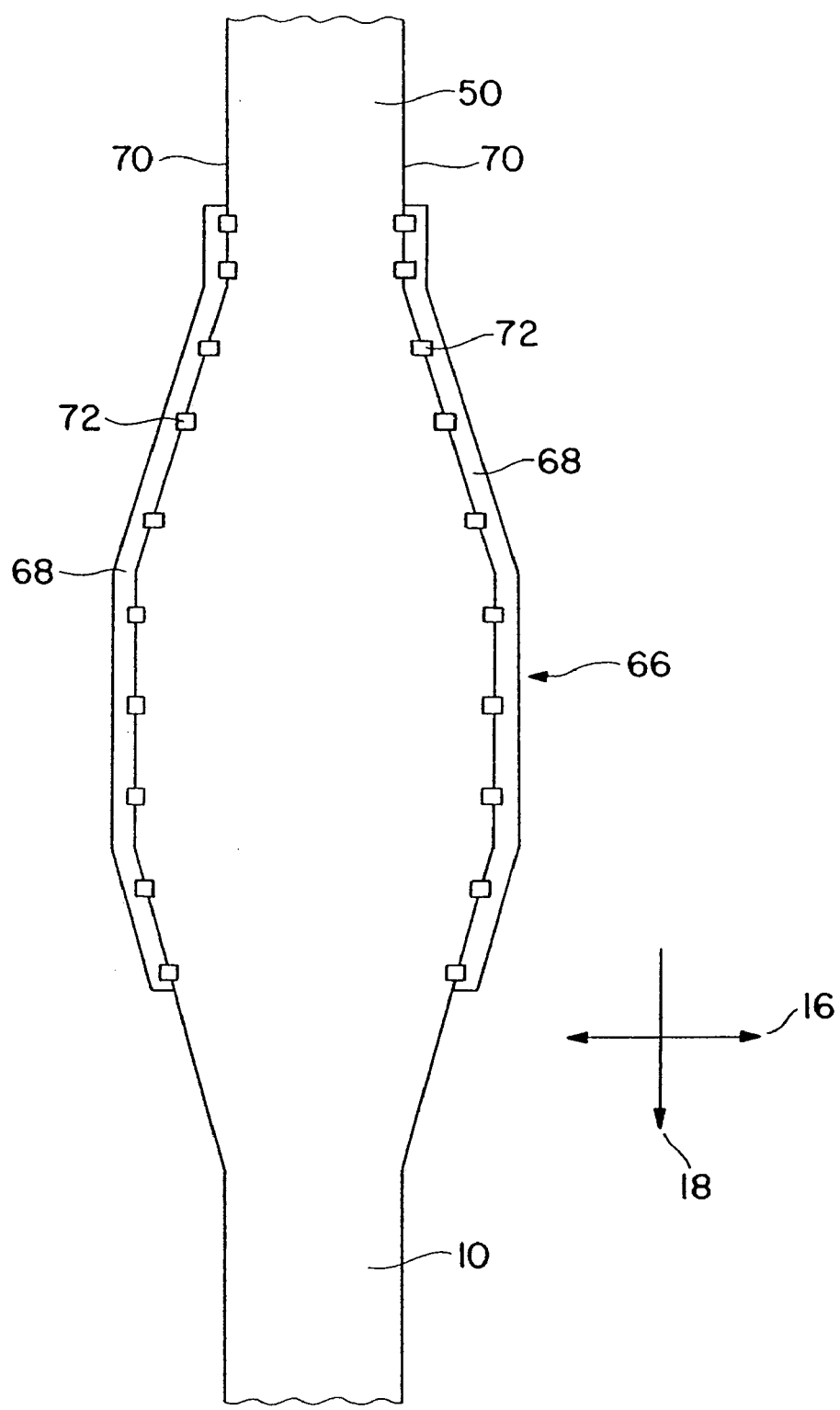
FIG. 4*a* is a top view of the tenter frame utilized in the process shown in FIG. 4.

Alternatively, as shown in FIG. 4a, the laminate 50 may be passed through a tenter frame 66 such that the laminate 50 is mechanically stretched in the cross direction 16 by at least about 50 percent, desirably by at least about 65 percent, more desirably by at least about 75 percent, most desirably by about 100 percent. Referring to FIG. 4b, the tenter frame 66 includes a pair of diverging belts or chains 68. The transverse edges 70 of the laminate 50 are attached to the diverging belts 68 by a series of clips 72 which hold the laminate 50 in place. As the laminate 50 is pulled through the tenter frame 66, the diverging belts 68 mechanically stretch the laminate 50 in the cross-direction 16 by a desired amount, suitably by at least about 50 percent. As the mechanically stretched laminate exits the tenter frame 66, the transverse edges 70 are released and the laminate is allowed to relax back toward its pre-stretched dimension thereby forming an extensible laminate 10 of the present invention. Other means known in the art may also be used to mechanically stretch the laminate 50 in the cross-direction by at least about 50 percent.

EXAMPLES

Laminates including a layer of an extensible nonwoven web and an elastic film where prepared as follows.

Sample 1:

Extensible laminates were prepared by thermally laminating a 0.75-osy (approximately 25.4 gsm) spunbond web to either side of a 35 gsm elastomeric sheet. The spunbond web, produced by Kimberly-Clark Corporation, was necked to provide a percent neckdown of about 56 percent. The elastomeric sheet was a MD-6659 film obtained from Kraton Polymers of Houston, Tex.

The laminates were mechanically stretched in the cross direction by about 100 percent to produce an extensible laminate of the present invention. The extensible laminates were cycle tested to measure the elongation/retraction ratio, hysteresis value and set of the extensible laminates immediately and at 1, 7 and 19 days after stretching. An unstretched control laminate was also tested. The results are included in Table 1.

TABLE 1

| Code | E/R Ratio | % Decrease | Hysteresis (%) | % Decrease | Set (%) | % Decrease |
|---|---|---|---|---|---|---|
| Un-stretched | 3.26 | | 50 | | 9 | |
| Stretched | 2.36 | 27.6 | 40 | 20 | 7 | 22 |
| Day 1 | 2.37 | 27.3 | 39 | 22 | 8 | 11 |
| Day 7 | 2.49 | 23.6 | 41 | 18 | 8 | 11 |
| Day 19 | 2.43 | 25.5 | 41 | 18 | 8 | 11 |

The percent decrease for the E/R ratio, hysteresis value and set may be calculated as follows:

% Decrease=[(unstretched−stretched)/(unstretched)]×100.

For example, the decrease in the E/R ratio on Day 1 would be calculated as [(3.26-2.36)/3.26]×100=27.3%.

Sample 2:

Extensible laminates were prepared by thermally laminating a 0.5-osy (approximately 17 gsm) spunbond web to either side of a 42 gsm elastomeric sheet. The spunbond web, produced by Kimberly-Clark Corporation, was necked from a width of about 126 inches (about 320 centimeters) to a width of about 45 inches (about 114.3 centimeters) to provide a percent neckdown of about 64 percent. The elastomeric sheet was a KRATON G-2755 film obtained from Kraton Polymers of Houston Tex.

The laminates were mechanically stretched in the cross direction by about 100 percent to produce an extensible laminate of the present invention. The extensible laminates were cycle tested to measure the elongation/retraction ratio, hysteresis value and set of the extensible laminates immediately and at 7, 19 and 26 days after stretching. An unstretched control laminate was also tested. The results are shown in Table 2.

TABLE 2

| Code | E/R Ratio | % Decrease | Hysteresis (%) | % Decrease | Set (%) | % Decrease |
|---|---|---|---|---|---|---|
| Un-stretched | 2.88 | | 49 | | 9 | |
| Stretched | 2.01 | 30.2 | 36 | 26.5 | 6 | 33 |
| Day 7 | 2.19 | 24.0 | 39 | 20.4 | 7 | 22 |
| Day 19 | 2.18 | 24.3 | 38.5 | 21.4 | 8 | 11 |
| Day 26 | 2.19 | 24.0 | 39 | 20.4 | 7 | 22 |

TEST FOR DETERMINING HYSTERESIS, SET AND ELONGATION/RETRACTION RATIO

The cycling test is a method, using a constant-rate-of-extension tensile tester such as, for example, Sintech 2, Model 3397-139, available from Sintech Corporation, Cary, N.C., to determine the elastic properties of an extensible laminate. Specifically, a sample of an extensible laminate is cut to a 4.5×3 inch dimension, the 4.5 inches being in the cross-direction. The 3-inch long sample is clamped between two pneumatic jaws so that the gauge length (jaw separation) is two inches, and the direction of pull is in the cross-direction. The pulling speed is 20 inches/min. Testing is done during two extension/retraction cycles. The sample is first pulled to 100% elongation (4-inch jaw separation) and immediately returned (retracted) to the starting gauge length. The extension-retraction cycle is then repeated. Finally, the sample is pulled to an extension where it breaks, at which time the test is stopped. Force and extension are measured by an appropriate load cell and other sensors. Data are recorded and analyzed by a computer program.

The hysteresis was calculated by subtracting the energy recovered during the first cycle retraction from the energy delivered to extend the material in the first cycle extension, this quantity divided by the energy delivered to extend the material in the first cycle extension, this quantity times 100. The energy delivered and the energy recovered were determined by the computer and measured as the area under the stress strain curve.

The percent set is determined by measuring the extension that the sample is at during the retraction cycle when the force first measures 10 grams or lower. The percent set is defined as the maximum extension length the sample is taken to minus the length determined in the 10 gram retraction measurement above, this quantity divided by the maximum extension length, this quantity times 100.

The elongation/retraction ratio (E/R ratio) of the extensible laminate is characterized by the load (force) measured at 30% elongation during the first cycle extension (pull) cycle and the load at 30% elongation during the second cycle retraction mode. The E/R ratio measurement is reported as a ratio of retraction force per extension force times 100.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An extensible laminate comprising:
a necked nonwoven web; and
an elastomeric sheet,
wherein the necked nonwoven web and the elastomeric sheet after lamination and prior to a cycling test, have been mechanically stretched in the cross direction to provide an extensible laminate having a hysteresis value, measured during a first 100 percent elongation/retraction cycle of the cycling test, at least about 15 percent lower than a comparable extensible laminate that has not been previously stretched.

2. The extensible laminate of claim 1, wherein the extensible laminate has a hysteresis value at least about 20 percent lower than a comparable extensible laminate that has not been previously stretched.

3. The extensible laminate of claim 1, wherein the extensible laminate has a 7-day hysteresis value at least about 15 percent lower than a comparable extensible laminate that has not been previously stretched.

4. The extensible laminate of claim 1, wherein the extensible laminate has a 30-day hysteresis value at least about 15 percent lower than a comparable extensible laminate that has not been previously stretched.

5. The extensible laminate of claim 1, wherein the extensible laminate has a lower elastic set value than a comparable extensible laminate that has not been previously stretched.

6. The extensible laminate of claim 1, wherein the extensible laminate has an elastic set value at least about 10 percent lower than a comparable extensible laminate that has not been previously stretched.

7. The extensible laminate of claim 1, wherein the extensible laminate has an elastic set value at least about 20 percent lower than a comparable extensible laminate that has not been previously stretched.

8. The extensible laminate of claim 1, wherein the extensible laminate has an elastic set value at least about 30 percent lower than a comparable extensible laminate that has not been previously stretched.

9. The extensible laminate of claim 1, wherein the extensible laminate has a lower elongation/retraction ratio than a comparable extensible laminate that has not been previously stretched.

10. The extensible laminate of claim 1, wherein the extensible laminate has an elongation/retraction ratio at least about 15 percent lower than a comparable extensible laminate that has not been previously stretched.

11. The extensible laminate of claim 1, wherein the extensible laminate has an elongation/retraction ratio at least about 20 percent lower than a comparable extensible laminate that has not been previously stretched.

12. The extensible laminate of claim 1, wherein the extensible laminate has an elongation/retraction ratio at least about 25 percent lower than a comparable extensible laminate that has not been previously stretched.

13. The extensible laminate of claim 1, wherein the extensible laminate has a 7-day elongation/retraction ratio at least about 15 percent lower than a comparable extensible laminate that has not been previously stretched.

14. The extensible laminate of claim 1, wherein the extensible laminate has a 30-day elongation/retraction ratio at least about 20 percent lower than a comparable extensible laminate that has not been previously stretched.

15. The extensible laminate of claim 1, wherein the elastomeric sheet comprises a film including a styrene copolymer selected from styrene-butadiene-styrene, styrene-isoprene-styrene, styrene-ethylene/butylene-styrene, styrene-ethylene/propylene-styrene and combinations thereof.

16. The extensible laminate of claim 1, wherein the elastomeric sheet comprises a film including a single-site catalyzed ethylene-alpha olefin copolymer having a density of about 0.860 to about 0.900 grams per cubic centimeter.

17. The extensible laminate of claim 1, wherein the elastomeric sheet comprises a breathable elastomeric film.

18. An extensible laminate comprising:
a necked nonwoven web; and
an elastomeric sheet,
wherein the necked nonwoven web and the elastomeric sheet, after lamination and prior to a cycling test, have been mechanically stretched in the cross direction to provide an extensible laminate having an elastic set value, measured during a first 100 percent elongation/retraction cycle of the cycling test, at least about 10 percent lower than a comparable extensible laminate that has not been previously stretched.

19. The extensible laminate of claim 18, wherein the extensible laminate has an elastic set value at least about 20 percent lower than a comparable extensible laminate that has not been previously stretched.

20. The extensible laminate of claim 18, wherein the extensible laminate has an elastic set value at least about 30 percent lower than a comparable extensible laminate that has not been previously stretched.

21. The extensible laminate of claim 18, wherein the extensible laminate has a 7-day elastic set value at least about 10 percent lower than a comparable extensible laminate that has not been previously stretched.

22. The extensible laminate of claim 18, wherein the extensible laminate has a 30-day elastic set value at least about 10 percent lower than a comparable extensible laminate that has not been previously stretched.

23. The extensible laminate of claim 18, wherein the extensible laminate has a lower hysteresis value than a comparable extensible laminate that has not been previously stretched.

24. The extensible laminate of claim 18, wherein the extensible laminate has a lower elongation/retraction ratio than a comparable extensible laminate that has not been previously stretched.

25. The extensible laminate of claim 18, wherein the extensible laminate has an elongation/retraction ratio at least about 20 percent lower than a comparable extensible laminate that has not been previously stretched.

26. The extensible laminate of claim 18, wherein the extensible laminate has a 7-day elongation/retraction ratio at least about 15 percent lower than a comparable extensible laminate that has not been previously stretched.

27. The extensible laminate of claim 18, wherein the extensible laminate has a 30-day elongation/retraction ratio at least about 15 percent lower than a comparable extensible laminate that has not been previously stretched.

28. The extensible laminate of claim 18, wherein the elastomeric sheet comprises a film including a styrene copolymer selected from styrene-butadiene-styrene, styrene-isoprene-styrene, styrene-ethylene/butylene-styrene, styrene-ethylene/propylene-styrene and combinations thereof.

29. The extensible laminate of claim 18, wherein the elastomeric sheet comprises a film including a single-site catalyzed ethylene-alpha olefin copolymer having a density of about 0.860 to about 0.900 grams per cubic centimeter.

30. The extensible laminate of claim 18, wherein the elastomeric sheet comprises a breathable elastic film.

31. The extensible laminate of claim 1, wherein the extensible laminate is breathable.

32. The extensible laminate of claim 1, wherein the necked nonwoven web comprises a multilayer nonwoven web.

33. The extensible laminate of claim 1, wherein the elastomeric sheet comprises a filled elastomeric sheet.

34. The extensible laminate of claim 1, further comprising an additional extensible nonwoven web, wherein the elastomeric sheet is disposed between the reversibly necked nonwoven web and the additional extensible nonwoven web.

35. The extensible laminate of claim 1, wherein the necked nonwoven web and the elastomeric sheet after lamination have been mechanically stretched in the cross direction by at least about 50 percent.

36. The extensible laminate of claim 1, wherein the necked nonwoven web and the elastomeric sheet after lamination have been mechanically stretched in the cross direction by at least about 65 percent.

37. The extensible laminate of claim 1, wherein the necked nonwoven web and the elastomeric sheet after lamination have been mechanically stretched in the cross direction by at least about 75 percent.

38. The extensible laminate of claim 1, wherein the necked nonwoven web and the elastomeric sheet after lamination have been mechanically stretched in the cross direction by at least about 100 percent.

39. The extensible laminate of claim 18, wherein the extensible laminate is breathable.

40. The extensible laminate of claim 18, wherein the necked nonwoven web comprises a multilayer nonwoven web.

41. The extensible laminate of claim 18, wherein the elastomeric sheet comprises a filled elastomeric sheet.

42. The extensible laminate of claim 18, further comprising an additional extensible nonwoven web, wherein the elastomeric sheet is disposed between the reversibly necked nonwoven web and the additional extensible nonwoven web.

43. The extensible laminate of claim 18, wherein the necked nonwoven web and the elastomeric sheet after lamination have been mechanically stretched in the cross direction by at least about 50 percent.

44. The extensible laminate of claim 18, wherein the necked nonwoven web and the elastomeric sheet after lamination have been mechanically stretched in the cross direction by at least about 65 percent.

45. The extensible laminate of claim 18, wherein the necked nonwoven web and the elastomeric sheet after lamination have been mechanically stretched in the cross direction by at least about 75 percent.

46. The extensible laminate of claim 18, wherein the necked nonwoven web and the elastomeric sheet after lamination have been mechanically stretched in the cross direction by at least about 100 percent.

\* \* \* \* \*